US 11,159,900 B2

(12) United States Patent
Hamacher et al.

(10) Patent No.: US 11,159,900 B2
(45) Date of Patent: Oct. 26, 2021

(54) BIMODAL HEARING STIMULATION SYSTEM

(71) Applicant: ADVANCED BIONICS AG, Staefa (CH)

(72) Inventors: Volkmar Hamacher, Hannover (DE); Josef Chalupper, Paunzhausen (DE)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 16/495,386

(22) PCT Filed: Mar. 20, 2017

(86) PCT No.: PCT/EP2017/056540
§ 371 (c)(1),
(2) Date: Sep. 18, 2019

(87) PCT Pub. No.: WO2018/171858
PCT Pub. Date: Sep. 27, 2018

(65) Prior Publication Data
US 2020/0077212 A1    Mar. 5, 2020

(51) Int. Cl.
*H04R 25/00* (2006.01)
*A61N 1/36* (2006.01)

(52) U.S. Cl.
CPC ......... *H04R 25/70* (2013.01); *A61N 1/36038* (2017.08); *H04R 25/606* (2013.01)

(58) Field of Classification Search
CPC ............ A61N 1/36036; A61N 1/36038; A61N 1/36039
See application file for complete search history.

(56) References Cited

U.S. PATENT DOCUMENTS

| 6,231,604 B1 | 5/2001 | Von Ilberg |
| 7,769,467 B1 | 8/2010 | Emadi et al. |

(Continued)

FOREIGN PATENT DOCUMENTS

| WO | 2011032021 | 3/2011 |
| WO | 2013142843 | 9/2013 |

(Continued)

OTHER PUBLICATIONS

International Search Report and Written Opinion received in International Application No. PCT/US17/56540.

*Primary Examiner* — Ryan Robinson
(74) *Attorney, Agent, or Firm* — ALG Intellectual Property, LLC

(57) ABSTRACT

A bimodal hearing stimulation system comprises an implantable stimulation assembly for applying neural stimulation to a patient's hearing according to an electrical stimulation signal; an acoustic stimulation unit for applying acoustic stimulation to the patient's hearing according to an acoustic stimulation signal; and a sound processor for generating the electric stimulation signal and the acoustic stimulation signal from an input audio signal. The sound processor is configured to divide the input audio signal into a plurality of frequency bands. The sound processor comprises a weighting unit for dynamically determining for each of the frequency bands a relative loudness weight of the electric stimulation and a relative loudness weight of the acoustic stimulation as a function of the present level of the input audio signal in the respective frequency band. The sound processor is configured to apply the weighting function when generating the electric stimulation signal and the acoustic stimulation signal.

19 Claims, 7 Drawing Sheets

(56) References Cited

U.S. PATENT DOCUMENTS

| | | | |
|---|---|---|---|
| 8,265,765 B2* | 9/2012 | Nicolai | H04R 25/70 |
| | | | 607/55 |
| 9,731,129 B2* | 8/2017 | Polak | A61N 1/025 |
| 10,721,574 B2* | 7/2020 | Polak | A61N 1/36036 |
| 2006/0287690 A1 | 12/2006 | Bouchataoui et al. | |
| 2013/0272556 A1* | 10/2013 | Hamacher | H04R 25/50 |
| | | | 381/328 |
| 2015/0012053 A1 | 1/2015 | Downing | |
| 2016/0184586 A1* | 6/2016 | Okuyama | A61N 1/36038 |
| | | | 607/57 |
| 2016/0235986 A1 | 8/2016 | Murad et al. | |
| 2017/0072197 A1 | 3/2017 | Alfsmann | |
| 2017/0128723 A1* | 5/2017 | Hamacher | A61N 1/36128 |
| 2018/0050202 A1* | 2/2018 | Busby | H04R 25/353 |

FOREIGN PATENT DOCUMENTS

| | | | | |
|---|---|---|---|---|
| WO | 2015018457 | | 2/2015 | |
| WO | 2016004970 | | 1/2016 | |
| WO | WQ-2016004970 A1 * | | 1/2016 | H04R 25/35 |
| WO | 2017033139 | | 3/2017 | |

\* cited by examiner

BIMODAL HEARING STIMULATION SYSTEM

The invention relates to a bimodal hearing stimulation system comprising an implantable stimulation assembly, such as a cochlear implant, for applying neural stimulation to the patient's hearing according to an electrical stimulation signal, an acoustic stimulation unit, such as a hearing aid, for applying acoustic stimulation to the patient's hearing according to an acoustic stimulation signal, and a sound processor for generating the electric stimulation signal and the acoustic stimulation signal from an input audio signal, which is usually captured by a microphone arrangement from ambient sound.

Typically, such bimodal systems combine neural stimulation, e.g. by a cochlear implant and acoustic stimulation. Cochlear implants comprise an electrode array for electrical stimulation of the cochlear at various stimulation sites determined by the position of the respective electrode. Typical systems for bimodal stimulation of the hearing comprise a cochlear implant at the ipsilateral ear and a device for acoustic stimulation of the ipsilateral ear or the contralateral ear. Systems with electric and acoustic stimulation of the same ear are also known as hybrid devices or EAS devices. In systems with contralateral acoustic stimulation the acoustic stimulation device typically is an (electro-acoustic) hearing aid; alternatively, acoustic stimulation can be achieved by a bone conduction hearing aid.

For fitting a bimodal stimulation device a fitting device is connected to the electric stimulation device and the acoustic stimulation device in order to adjust the respective stimulation parameters individually so as to optimize the hearing impression of the patient. In a relatively simple model, the impact of the stimulation parameters may be described by the input/output (I/O) curves of the electric stimulation and the acoustic stimulation. For acoustic stimulation, the I/O curve represents the output level provided by the loudspeaker as the function of the input sound level at the microphone; the acoustic stimulation I/O curves vary as a function of the frequency (or the frequency band) of the audio signal (in a hearing instrument, the input audio signals are divided into various frequency channels for further signal processing). For electrical stimulation, the I/O curves represent the stimulation current for each stimulation channel (e.g. for each stimulation electrode) as a function of the input sound level at the microphone.

Due to improved surgical techniques, nowadays more and more cochlear implant (CI) patients have useful residual acoustic hearing after surgery, so that the number of patients who may benefit from bimodal, e.g. both electric and acoustic, stimulation presently is increasing. Typically, the acoustic frequency range is divided into a first subrange for acoustic stimulation and another subrange for electric stimulation in order to avoid an overlap of both stimulation modalities, since usually an overlap between electric and acoustic stimulation may degrade signal quality and/or speech understanding and thus is not desirable. Typically, the crossover frequency between acoustic stimulation and electric stimulation is determined based on the patient's acoustic audiogram, for example taken at 70 dB HL.

U.S. Pat. No. 6,231,604 B1 relates to an EAS system wherein the electrical stimulation signal is representative of a first subrange of audio frequencies and wherein the acoustic stimulation signal is representative of a second subrange of audio frequencies.

US 2006/0287690 A1 relates to an EAS system wherein a delay is imposed on at least one of the acoustic signal delivery path and the electrical signal delivery path so that the electrical stimulation is provided to the cochlea at a desired time relative to a time of arrival of acoustic stimuli at the cochlea; thereby the frequency range of a received sound represented by the electrical stimulation is received simultaneously with the frequency range of the received sound represented by the acoustic stimulation.

U.S. Pat. No. 7,769,467 B1 relates to a CI system wherein compensating current is applied to affect the excitation field caused by the stimulation current via at least one additional electrode, and wherein the compensating current is dynamically adjusted as a function of an amplitude of the stimulation current.

WO 2013/142843 A1 relates to an EAS system which is fitted based on measurements of the interaction of acoustic and electric stimulation.

US 2016/0235986 A1 relates to an EAS system which may switch back and forth between an acoustic-only mode employing acoustic stimulation only and an EAS-mode implying both acoustic and electric stimulation; reasons for using the acoustic-only mode may be that the EAS system is in a post-implant time period or that an event has occurred which prevents the CI device from applying electrical stimulation, for example that the headpiece is connected from the sound processor.

US 2015/0012053 A1 relates to an EAS system wherein in an EAS stimulation mode the apical electrodes are disabled for standard electrical stimulation and may be temporarily enabled for applying conditioning stimulation when a certain event is detected. Sub-threshold electrical stimulation may be applied to the patient by way of one or more electrodes disposed within an apical region of the cochlea together with the application of acoustic stimulation; such sub-threshold stimulation may be provided additionally or alternatively to the condition stimulation. The sub-threshold stimulation may have a variable stimulation level depending on a sound level of the detected audio content; for example, the sub-threshold stimulation level may be based on a predetermined percentage of the sound level of the detected audio content. The EAS system may switch from the EAS mode to an electrical-only stimulation mode once the patient loses the residual hearing.

WO 2016/004970 A1 relates to an EAS system wherein the crossover frequency between acoustic stimulation and electric stimulation is changed as a function of time during an acclimatization period.

It is an object of the invention to provide for a bimodal hearing stimulation system which is particularly suitable for patients with relatively pronounced residual acoustic hearing. It is a further object to provide for a corresponding bimodal stimulation method. It is a still further object of the invention to provide for a fitting method for such bimodal stimulation system.

According to the invention, these objects are achieved by a bimodal stimulation system, a bimodal stimulation method and a fitting method as described herein.

The invention is beneficial in that, by dynamically determining a relative loudness weight of the electric stimulation and a relative loudness weight of the acoustic stimulation for each frequency band as a function of the present level of the input audio signal in the respective frequency band, the utilization of the residual acoustic hearing of the patient can be optimized due to the input level dependent selection of acoustic or electric stimulation in each frequency band, so that the bimodal stimulation can be optimized for the present use situation. Preferably, the sound processor is configured to select one stimulation program from a plurality of stimulation programs according to a present acoustic situation, with the weight function depending on the presently selected stimulation program by the sound processor, thereby further optimizing bimodal stimulation for the present use situation.

For example, at low input levels acoustic amplification often is not sufficient to ensure audibility, so that electric stimulation is superior, while at high input levels, however, usually acoustic stimulation is superior as it allows to success temporal fine structure cues and provides better spectral and temporal resolution, so that speech understanding in noisy situations and spatial listening may be improved.

For music, acoustic stimulation is preferable as the harmonic structure of music may be thereby preserved. However, in situations with acoustic feedback, electric stimulation may be preferable. On the other hand, in case of low battery power, acoustic-only stimulation may be preferable since it is more power-efficient than electric stimulation.

Preferred embodiments of the invention are defined in the dependent claims.

Hereinafter, examples of the invention will be illustrated by reference to the attached drawings, wherein.

Figure 1:
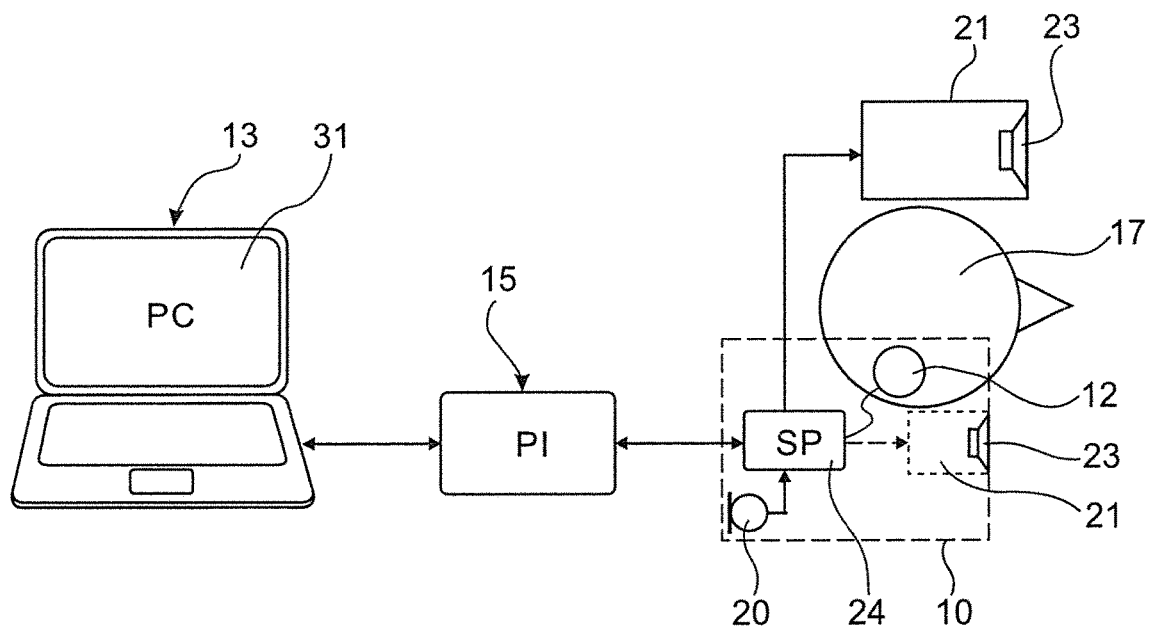
FIG. 1 is a schematic representation of an example of a system to be used in the invention.

FIG. 1 is a schematic representation a bimodal stimulation system, which, according to one example (shown in dashed lines), may be implemented as a EAS device 10 to be worn at one of the ears of a patient 17 (e.g. at the ipsilateral ear), comprising a microphone 20 for capturing input audio signals from ambient sound, a sound processor 24 for generating an electric stimulation signal and an acoustic stimulation signal from the input audio signal, an acoustic stimulation unit 21 comprising a loudspeaker 23 for acoustic stimulation of the ipsilateral ear according to the acoustic stimulation signal and an implantable stimulation assembly 12 for electric stimulation of the cochlea of the contralateral ear according to the electric stimulation signal.

According to an alternative example shown in FIG. 1, the ipsilateral device is for electric stimulation of the ipsilateral ear only (i.e. the device 10 in this case does not include the acoustic stimulation unit 21 but rather only the microphone 20, the sound processor 24 and the implantable stimulation assembly 12, while the acoustic stimulation unit 21 is implemented as a separate device to be worn at the contralateral ear for acoustic stimulation of the contralateral ear, with the acoustic stimulation unit 21 being connected to the sound processor 24 for receiving the acoustic stimulation signal; such variant may be beneficial, for example, for patients suffering from "binaural interference").

Figure 2:
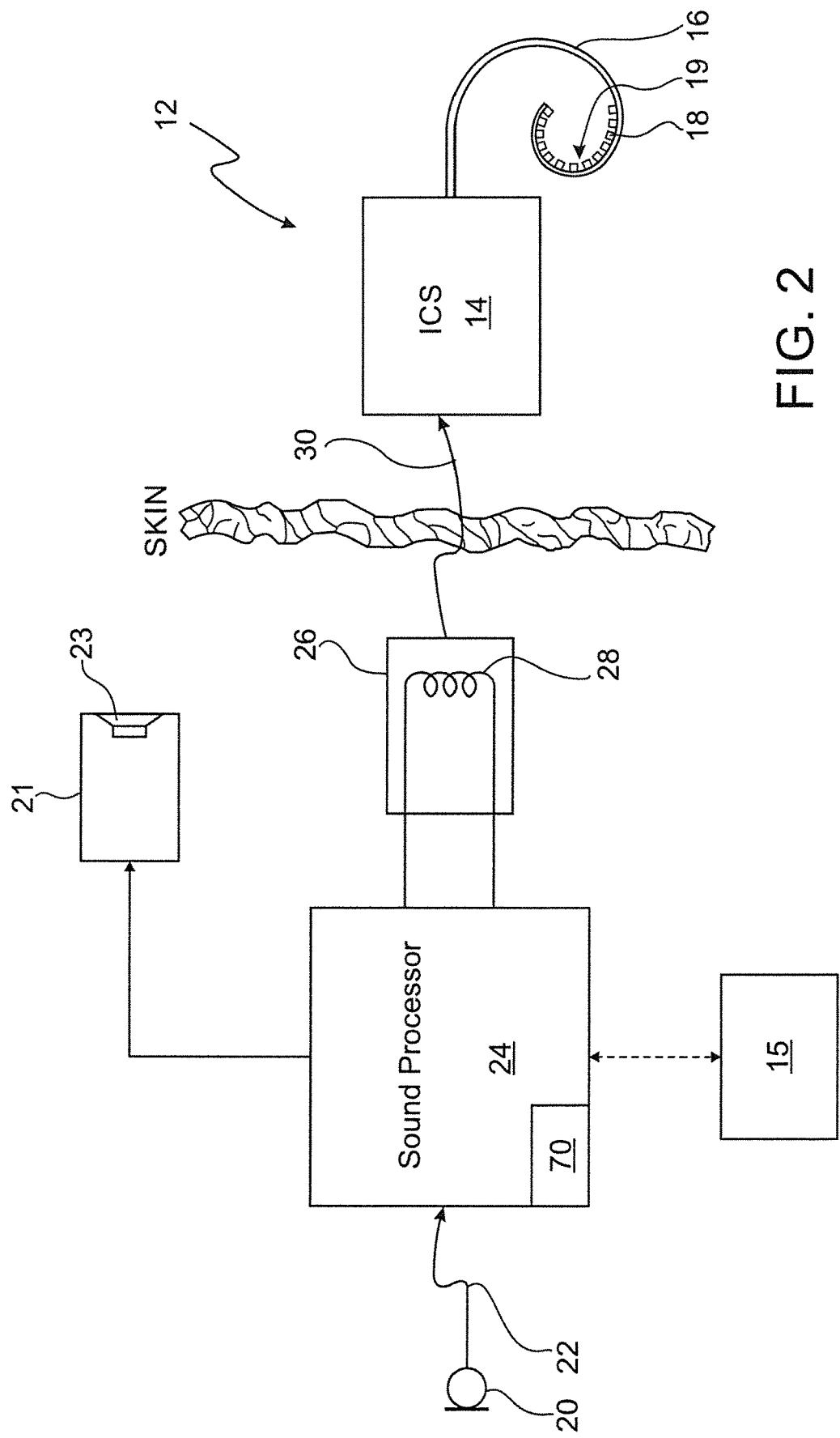
FIG. 2 is a schematic representation wherein the electric stimulation part of the system of FIG. 1 is shown in more detail.

In FIG. 2 the system of FIG. 1 is shown in some more detail. The sound processor 24 serves to detect or sense an audio signal and divide the audio signal into a plurality of analysis channels, each containing a frequency domain signal (or simply "signal") representative of a distinct frequency portion of the audio signal. A signal level value is determined for each analysis channel by analyzing the respective frequency domain signal Stimulation parameters are generated based on the frequency domain signal and are transmitted to the stimulation sub-system 12.

The implantable stimulation assembly 12 serves to generate and apply electrical stimulation (also referred to herein as "stimulation current" and/or "stimulation pulses") to stimulation sites at the auditory nerve within the cochlear of a patient 17 in accordance with the stimulation parameters received from the sound processor. Electrical stimulation is provided to the patient 17 via a CI stimulation assembly 18 comprising a plurality of stimulation channels. The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp-on time, and ramp-off time of the stimulation current that is applied to the stimulation site.

Figure 3:
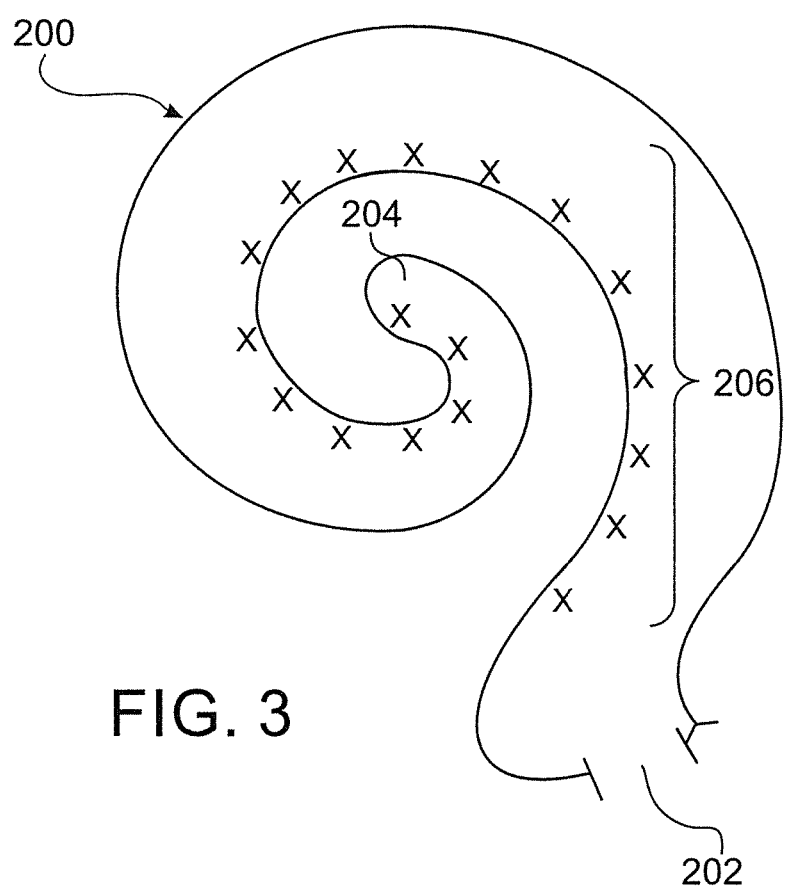
FIG. 3 is a schematic cross-section of a human cochlea with marked stimulation sites.

FIG. 3 illustrates a schematic structure of the human cochlea 200. As shown in FIG. 3, the cochlea 200 is in the shape of a spiral beginning at a base 202 and ending at an apex 204. Within the cochlea 200 resides auditory nerve tissue 206 which is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. The implantable stimulation assembly 12 is configured to apply stimulation to different locations within the cochlea 200 (e.g., different locations along the auditory nerve tissue 206) to provide a sensation of hearing.

Returning to FIG. 2, sound processor 24 and implantable stimulation assembly 12 are configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels and threshold current levels (as will be discussed in more detail below), input dynamic range parameters, channel acoustic gain parameters, front and backend dynamic range parameters, current steering parameters, amplitude values, pulse rate values, pulse width values, polarity values, filter characteristics, and/or any other control parameter as may serve a particular application. In particular, the control parameters may include a frequency allocation table (FAT) which determines the respective frequency range allocated to a certain electrode.

In the example shown in FIG. 2, the implantable stimulation assembly 12 comprises an implantable cochlear stimulator ("ICS") 14, a lead 16 and the stimulation assembly 18 disposed on the lead 16. The stimulation assembly 18 comprises a plurality of "stimulation contacts" 19 for electrical stimulation of the auditory nerve. The lead 16 may be inserted within a duct of the cochlea in such a manner that the stimulation contacts 19 are in communication with one or more stimulation sites within the cochlea, i.e. the stimulation contacts 19 are adjacent to, in the general vicinity of, in close proximity to, directly next to, or directly on the respective stimulation site.

In the example shown in FIG. 2, the non-implanted part comprises the microphone 20 which captures audio signals from ambient sound, a microphone link 22, the sound processor 24 which receives audio signals from the microphone 20 via the link 22, and a headpiece 26 having a coil 28 disposed therein. The sound processor 24 is configured to process the captured audio signals in accordance with a selected sound processing strategy to generate appropriate stimulation parameters for controlling the ICS 14 and may include, or be implemented within, a behind-the-ear (BTE) unit or a portable speech processor ("PSP"). In the example of FIG. 2 the sound processor 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30. The link 30 may include a bidirectional communication link and/or one or more dedicated unidirectional communication links. According to an alternative embodiment, the sound processor 24 and the ICS 14 may be directly connected by wires.

Figure 4:
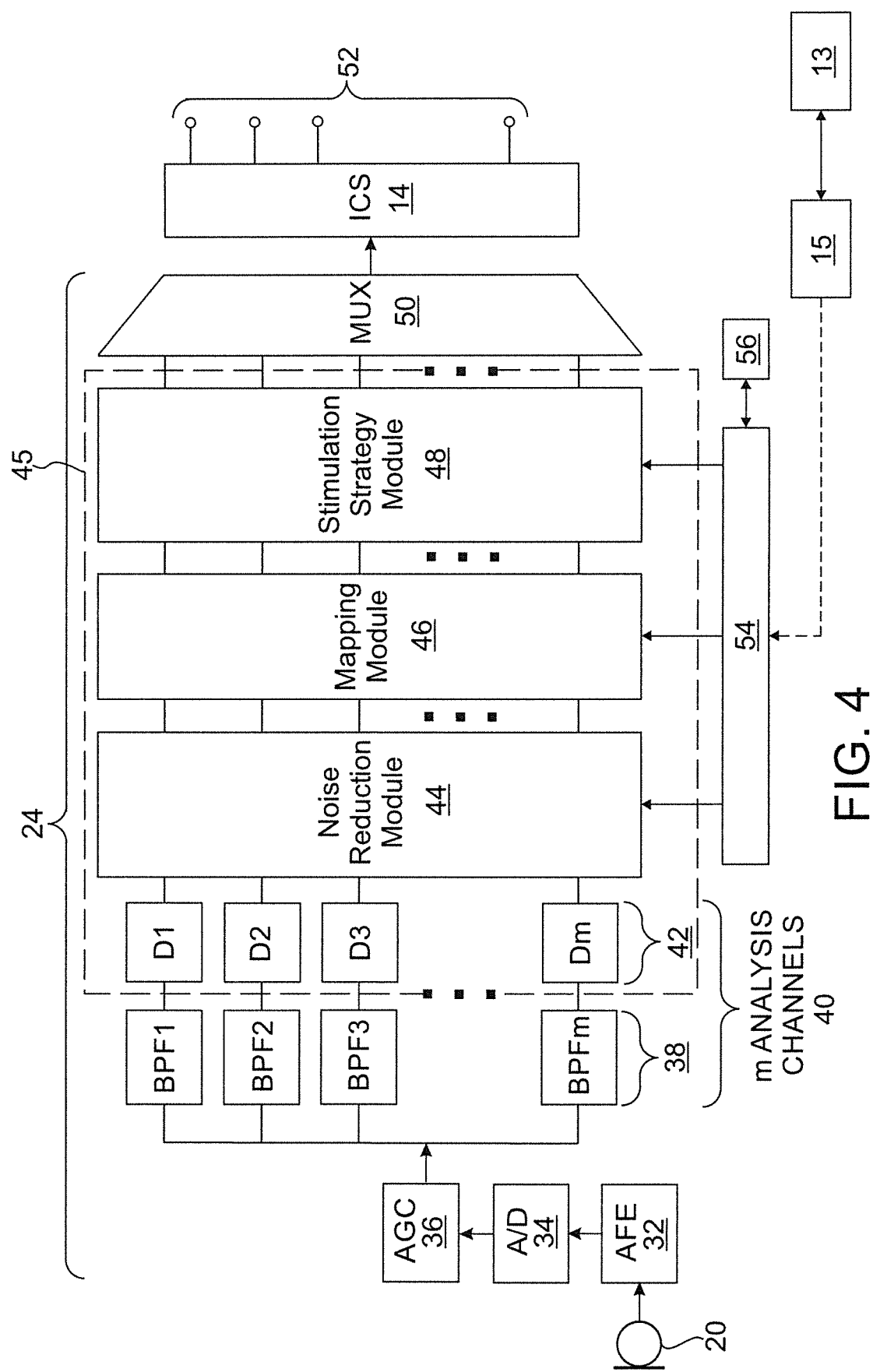
FIG. 4 is a block diagram of an example of the signal processing structure of a CI device to be used with the invention.

In FIG. 4 a schematic example of a sound processor 24 is shown. The audio signals captured by the microphone 20 are amplified in an audio front end circuitry 32, with the amplified audio signal being converted to a digital signal by an analog-to-digital converter 34. The resulting digital signal is then subjected to automatic gain control using a suitable automatic gain control (AGC) unit 36.

After appropriate automatic gain control, the digital signal is subjected to a filterbank 38 comprising a plurality of filters F1 . . . Fm (for example, band-pass filters) which are configured to divide the digital signal into m analysis channels 40, each containing a signal representative of a distinct frequency portion of the audio signal sensed by the microphone 20. For example, such frequency filtering may be implemented by applying a Discrete Fourier Transform to the audio signal and then distribute the resulting frequency bins across the analysis channels 40.

The signals within each analysis channel 40 are input into an envelope detector 42 in order to determine the amount of energy contained within each of the signals within the analysis channels 40 and to estimate the noise within each channel. After envelope detection the signals within the analysis channels 40 may be input into a noise reduction module 44, wherein the signals are treated in a manner so as to reduce noise in the signal in order to enhance, for example, the intelligibility of speech by the patient. Examples of the noise reduction module 44 are described in WO 2011/032021 A1.

The optionally noise reduced signals are supplied to a mapping module 46 which serves to map the signals in the analysis channels 40 to the stimulation channels S1 . . . Sn. For example, signal levels of the noise reduced signals may be mapped to amplitude values used to define the electrical stimulation pulses that are applied to the patient 17 by the ICS 14 via M stimulation channels 52. For example, each of the m stimulation channels 52 may be associated to one of the stimulation contacts 19 or to a group of the stimulation contacts 19.

The sound processor 24 further comprises a stimulation strategy module 48 which serves to generate one or more stimulation parameters based on the noise reduced signals and in accordance with a certain stimulation strategy (which may be selected from a plurality of stimulation strategies). For example, stimulation strategy module 48 may generate stimulation parameters which direct the ICS 14 to generate and concurrently apply weighted stimulation current via a plurality 52 of the stimulation channels S1 . . . Sn in order to effectuate a current steering stimulation strategy. Additionally or alternatively the stimulation strategy module 48 may be configured to generate stimulation parameters which direct the ICS 14 to apply electrical stimulation via only a subset N of the stimulation channels 52 in order to effectuate an N-of-M stimulation strategy.

The sound processor 24 also comprises a multiplexer 50 which serves to serialize the stimulation parameters generated by the stimulation strategy module 48 so that they can be transmitted to the ICS 14 via the communication link 30, i.e. via the coil 28.

The sound processor 24 may operate in accordance with at least one control parameter which is set by a control unit 54. Such control parameters, which may be stored in a memory 56, may be the most comfortable listening current levels (MCL), also referred to as "M levels", threshold current levels (also referred to as "T levels"), dynamic range parameters, channel acoustic gain parameters, front and back end dynamic range parameters, current steering parameters, amplitude values, pulse rate values, pulse width values, polarity values, the respective frequency range assigned to each electrode and/or filter characteristics.

Examples of such auditory prosthesis devices, as described so far, can be found, for example, in WO 2011/032021 A1.

Figure 5:
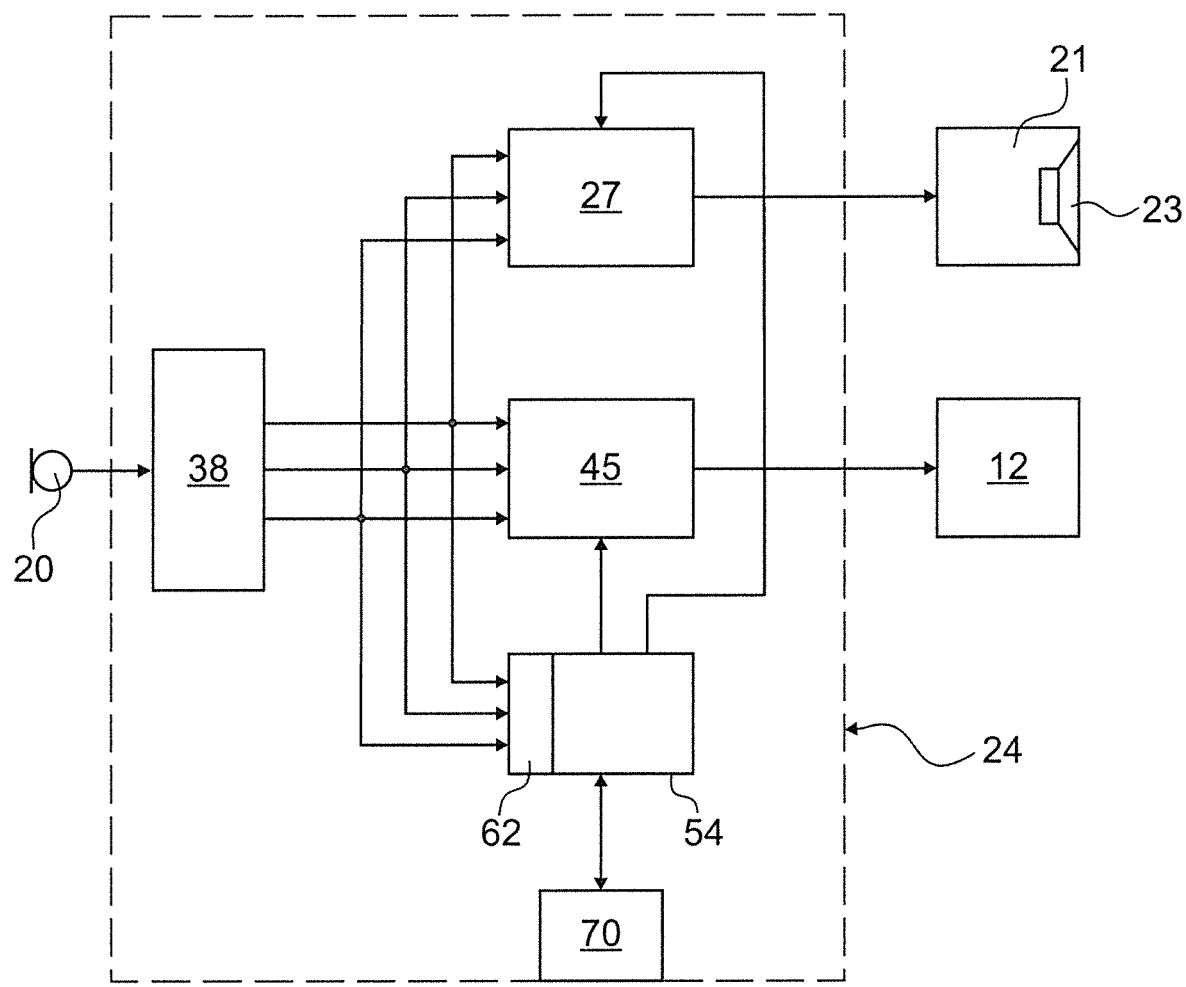
FIG. 5 is a block of an example of how a weighting feature of electric and acoustic stimulation may be implemented.

The sound processor 24 is configured to divide the input audio signal provided by the microphone 20 into a plurality of frequency bands, such as by using the filter bank 38, and to select one stimulation program from a plurality of stimulation programs according to the present acoustic situation. As illustrated in FIG. 5, which shows a schematic block diagram of an example of a bimodal system according to the invention, such program selection may occur automatically by using a classifier unit 62 which automatically determines the present acoustic situation by analyzing the input audio signal, or the stimulation program may be selected based on manual user input on a user interface 70 of the sound processor 24. The output of the filter bank 38 is supplied both to an audio signal processing unit 27 which generates the acoustic stimulation signal to be supplied to the output transducer 23 (which is usually a loudspeaker) and to a unit 45 for generating the electric stimulation signal supplied to the implantable stimulation assembly 12. A controller 54 is provided for controlling both the signal processing in the unit 27 and in the unit 45. The output of the filter bank 38 is also supplied to the controller 54 so as to enable dynamic control based on the present input audio signal. The controller 54 may comprise the classifier 52 and also may receive input from the user interface 70. As already mentioned above, the controller 54 may serve to select the stimulation program which is most appropriate for the present use situation of the system, in particular for the present acoustic situation as determined by the classifier 62.

In addition, the controller 54 may serve to realize a weighting unit for dynamically determining for each of the frequency bands a relative loudness weight of the electric stimulation and a relative loudness weight of the acoustic stimulation as a function of the present level of the input audio signal in the respective frequency band, with the weight function depending on the presently selected stimulation program. By acting on the signal processing unit 27 and 45, the controller 54 serves to apply the respective weighting function when generating the acoustic stimulation signal and the electric stimulation signal.

Figure 7:
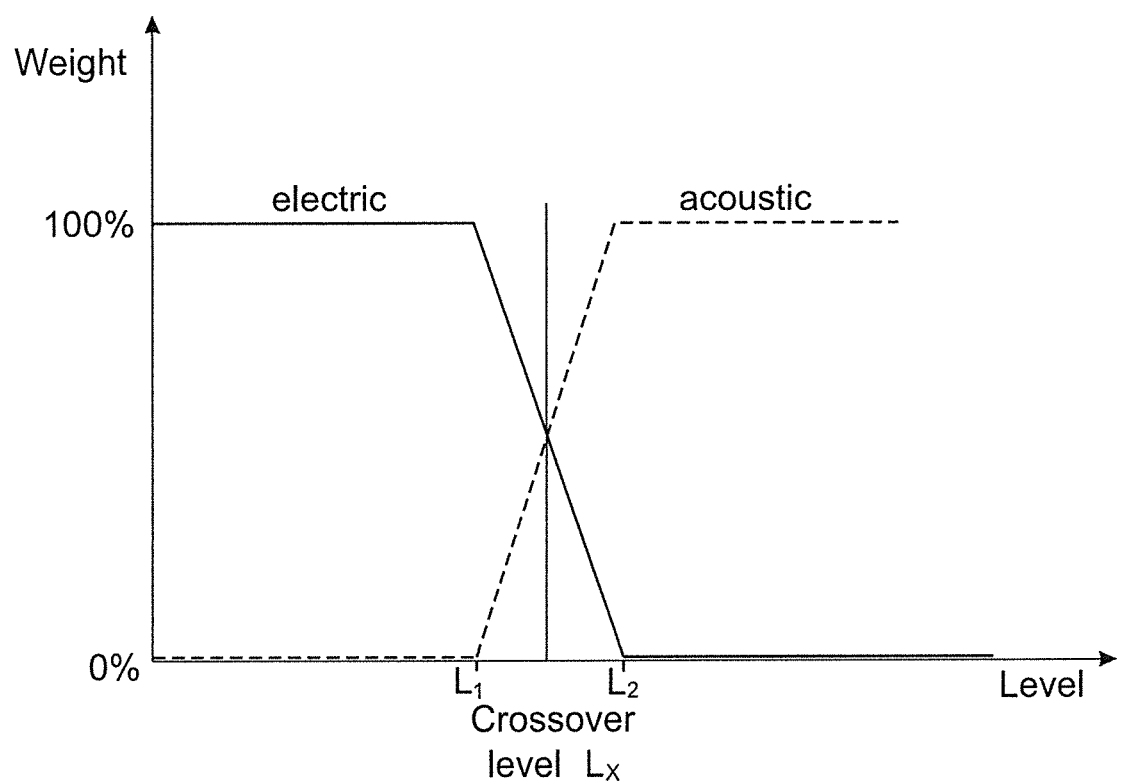
FIG. 7 is an example of a weighting function for electric and acoustic stimulation, wherein the respective weight is shown as a function of the input.

Preferably, in at least one of the stimulation programs the weight function for a bimodal frequency group comprising at least some of the frequency bands is such that, in terms of loudness, at input levels below a crossover level of the respective frequency band there is predominantly electric stimulation and at input levels above the crossover levels there is predominantly acoustic stimulation. An example of such weighting function is illustrated in FIG. 7, wherein the weight of the electric stimulation (solid line) and the weight of the acoustic stimulation (dashed line) is given as a function of the input signal level. In the example of FIG. 7, the acoustic stimulation weight is zero at input levels below a first threshold level $L_1$, which is lower than the crossover level $L_x$, and the electric stimulation weight is zero at input levels above a second threshold level $L_2$ which is higher than the crossover level $L_x$. Consequently, at input levels below the first threshold level $L_1$ the audible stimulation is electric stimulation only, and at input levels above the second threshold level $L_2$ the audible stimulation is acoustic stimulation only, while the first and second threshold levels $L_1$, $L_2$ define a level crossover range in between, in which the weight of the electric stimulation decreases from 100% to 0% and the weight of the acoustic stimulation increases from 0% to 100%, when the input level increases from the first threshold level $L_1$ to the second threshold level $L_2$, wherein at the crossover level $L_x$ the electric stimulation and the acoustic stimulation have an equal weight of 50%.

Figure 8:
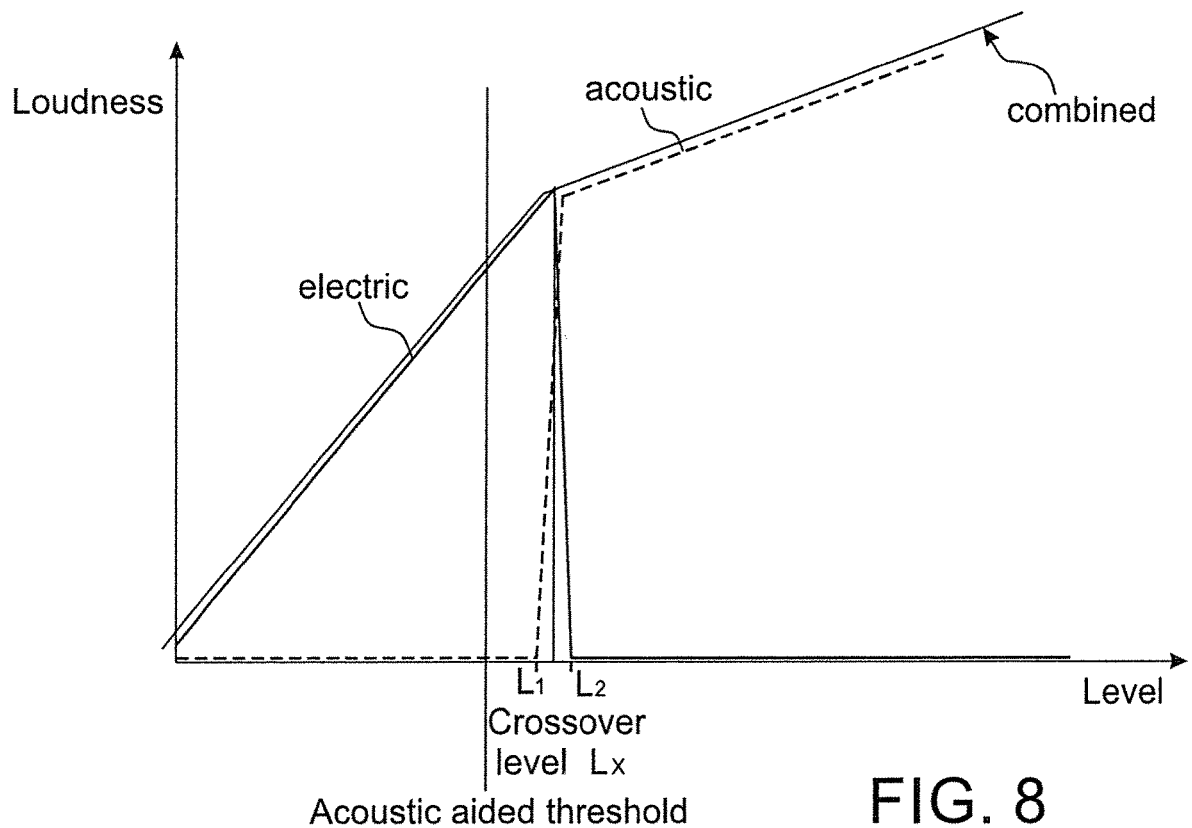
FIG. 8 is an example of the total loudness and the loudness contributions of the electric and acoustic stimulation in a given frequency band as a function of the input level.

For determining the relative loudness weights of the electric stimulation and the acoustic stimulation the weights of FIG. 7 are applied (by multiplying) to the respective electric input/output (I/O) function and to the respective acoustic I/O function, resulting in the respective loudness contributions of electric stimulation and acoustic stimulation as a function of the input level. In the example shown in FIG. 8, at input levels below $L_1$ the only loudness contribution is electric stimulation (i.e. there is no audible acoustic stimulation) and at input levels above $L_2$ the only loudness contribution is acoustic stimulation (i.e. there is no audible electric stimulation). The I/O functions may be standard electric and acoustic I/O functions. The weighting functions and the I/O functions preferably are such that at the crossover level $L_x$ the resulting weighted loudness is the same for electric stimulation and acoustic stimulation. Further, preferably, the weighting function is such that the total loudness, i.e. the sum of the loudness resulting from electric stimulation and the loudness resulting from acoustic stimulation, is a monotonous function of the input level, as illustrated in FIG. 8 (wherein the total loudness is shown by a thick solid line). This applies in particular to the crossover range between the levels $L_1$ and $L_2$. Typically, the total loudness resulting from acoustic and electric stimulation increases with increasing input level, as shown in FIG. 8, due to the shape of the underlying electric and acoustic I/O functions.

It is to be noted that the weighting concept relates to a weighting of electric and acoustic stimulation in terms of loudness so that a weight of 0% electric stimulation, for example, means that there is no audible electric stimulation, wherein 100% electric stimulation, for example, means that all of the audible stimulation is electric, while 50% electric stimulation and 50% acoustic stimulation means that electric stimulation and the acoustic stimulation provides for the same loudness.

Figure 6:
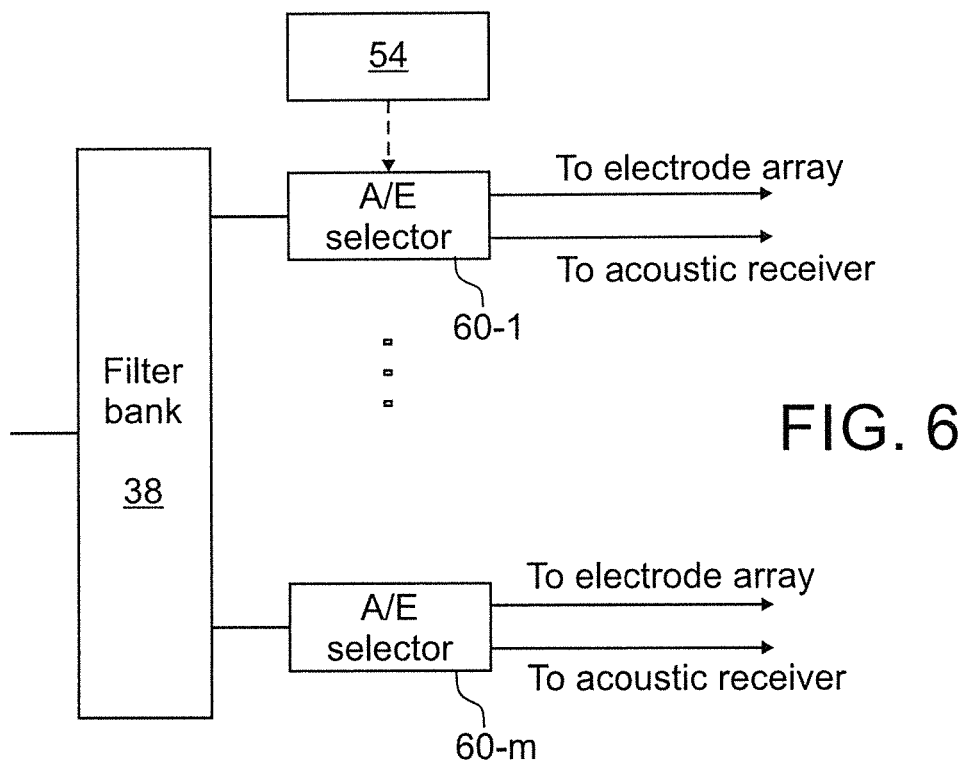
FIG. 6 is a block diagram for schematically illustrating the effect of a weighting function on signal processing.

FIG. 6 is a schematic illustration of the effect which a weighting function having the shape illustrated in FIG. 7 has on the signal processing. According to FIG. 6, the action of the weighting function may be illustrated by a unit 60-1, . . . , 60-m which is provided in each of the frequency bands/analysis channels generated by the filter bank 38 and which acts as a selector unit for selecting, depending on the input provided by the controller 54, electric stimulation or acoustic stimulation (or, if the input level falls within the crossover range between $L_1$ and $L_2$, a mixture of electric and acoustic stimulation).

Ideally, there is no crossover range at all, so as to avoid any overlap between electric and acoustic stimulation. However, in order to avoid gaps, a transition of the type shown in FIG. 7 may be necessary so as to provide for a smooth and monotonic transition entrance of loudness perception.

According to one example, there is no electric stimulation at all above the second threshold level $L_2$. However, according to an alternative example, there may be, at least for part of the level range above the second threshold level $L_2$ inaudible electric stimulation so as to support perception of the acoustic stimulation (since the weighting function relates to loudness weighting, the loudness weight for such inaudible electric stimulation still would be 0%, as shown in FIG. 7).

Figure 9:
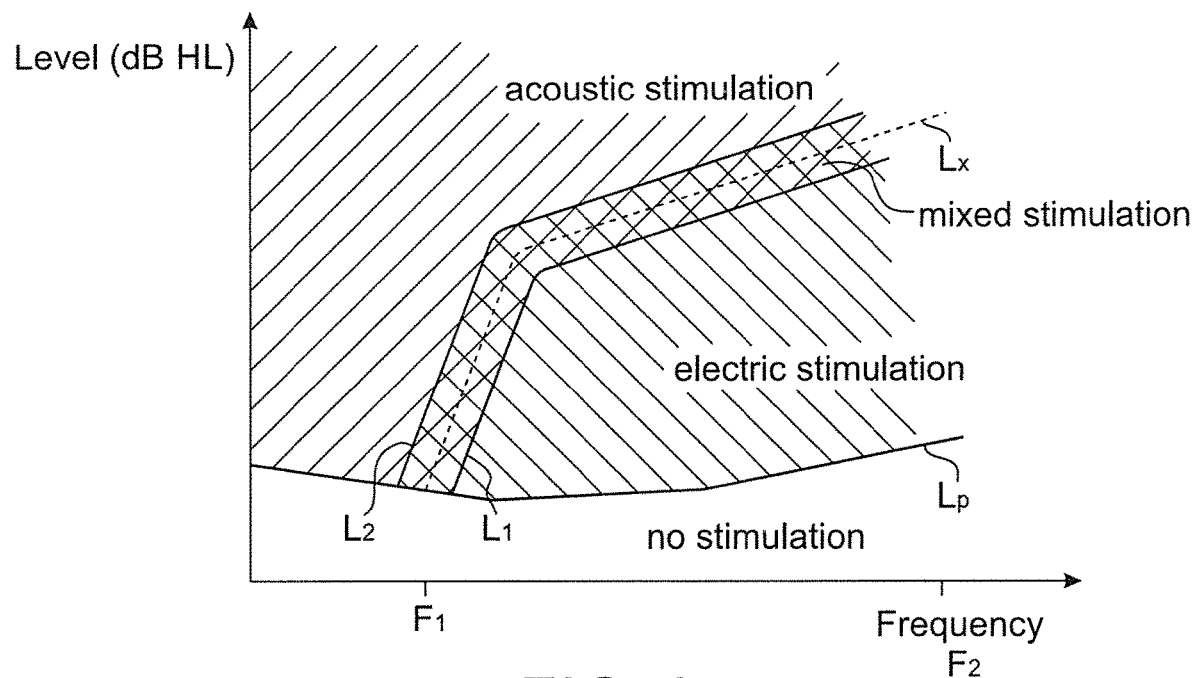
FIG. 9 is a diagram wherein the type of stimulation is shown as a function of frequency and audio signal input level.

While the examples of FIGS. 7 and 8 relate to a single one of the frequency bands, FIG. 9 is a diagram wherein the type of stimulation (acoustic stimulation/electric stimulation/mixed stimulation/no stimulation) is shown as a function of frequency (i.e. as a function of the center frequency of the frequency bands) and the input level. It can be seen that in the example of FIG. 9, which may be used for one of the stimulation programs, that for all frequencies there is no audible stimulation for input levels below a perception threshold level $L_p$; the specific value of the perception threshold level $L_p$ may slightly depend on frequency. For frequencies below a first threshold frequency $F_1$ there is for all input levels above the perception threshold level $L_p$ acoustic stimulation only but no audible electric stimulation (however, as in the case of the acoustic range above the second threshold level $L_2$ in FIGS. 7 and 8 there may be inaudible electric stimulation so as to support perception of the acoustic stimulation). The reason is that typically for patients with residual acoustic hearing at very low frequencies acoustic stimulation is more effective than electric stimulation even at low input levels.

For frequencies above the first threshold frequency $F_1$ there is audible electric stimulation (with no audible acoustic stimulation) for input levels above the perception threshold level $L_p$ and below the crossover level $L_x$ (or, as shown in FIG. 9, below the first threshold level $L_1$ in case that there is an overlap range), while at levels above the crossover level $L_x$ (or above the second threshold level $L_2$ in case that there is a crossover range, as illustrated in FIG. 9) there is acoustic stimulation (with no audible electric stimulation, which does not exclude inaudible electric stimulation, as discussed above). In case that there is a crossover range between $L_1$ and $L_2$, as illustrated in FIG. 9, there is a mixed stimulation region in which there is both electric and acoustic stimulation. The boundary between acoustic stimulation and electric stimulation is indicated by the dashed line in FIG. 9 which is labeled "$L_x$".

As can be seen in FIG. 9, the crossover level $L_x$ in this example increases with increasing frequency.

The frequency bands above the first threshold frequency $F_1$ may be considered to form a bimodal group, compared to the acoustic-only group of frequency bands below the threshold frequency $F_1$.

In some cases, there may be a third frequency range for frequencies above a second threshold frequency $F_2$ for which electric-only group wherein there is only audible electric stimulation but no audible acoustic stimulation. Such "electric stimulation only" may be selected whenever the aided acoustic threshold exceeds the maximum acoustic power output. Audiologically, however, even lower limits may make sense as a certain dynamic range is required for acoustic signal transmission without distortions (about 60 dB HL aided or 90 dB HL unaided).

Typically, the various stimulation programs specifically apply to a certain acoustic situation, like "music", "speech in noise", "speech in quiet", "feedback", etc., wherein the electric/acoustic stimulation weighting functions may be different for different stimulation programs.

For example, one of the stimulation programs may be a music program, which is selected for music input, wherein for at least some of the frequency bands, compared to a speech program which is selected for speech input, the relative loudness weight of the acoustic stimulation is increased and the relative loudness weight of the electric stimulation is reduced accordingly, since acoustic stimulation is more suitable than electric stimulation for preserving harmonic structures of music, with such enhancement of acoustic stimulation particularly applying for low input levels.

In acoustic situations, wherein at least for one frequency band there is residual feedback which cannot be suppressed by the usual acoustic feedback cancellation algorithms, a stimulation program may be selected which has a feedback elimination feature, wherein first, the crossover level in critical frequency band(s) is increased (which reduces the amount of required acoustic gain); if there is still feedback, the relative loudness weight of acoustic stimulation in the critical frequency band(s) is further reduced and the relative loudness weight of the electric stimulation in that frequency bands is increased accordingly, compared to the situation when no residual acoustic feedback is detected in the respective frequency band. Such feedback elimination feature may reduce the relative loudness weight of the acoustic stimulation at least temporarily to zero in case that such reduction is required for overcoming the feedback problem in the respective frequency band.

According to another example, one of the stimulation programs may be a low battery program which is selected in case that a low battery state of the system is detected, wherein at least in some of the frequency bands the relative loudness weight of the electric stimulation is reduced to zero for all input levels and the relative loudness weight of the acoustic stimulation is increased accordingly; in other words, the more power hungry electric stimulation is reduced in favor of the less power hungry acoustic stimulation. This implies that the amplification and the compression of the acoustic signal should be adjusted accordingly, so that the relevant input dynamic range, especially this soft sounds, are made acoustically audible to the user.

The crossed-over levels in all stimulation programs may be determined by a fitting device in a patient-specific manner depending on the individual hearing loss, the available acoustic gain and the feedback margin in the respective frequency band. The feedback margin may be determined by the fitting device, via an open-loop gain measurement. According to one example, the weighting functions, including the cross-over levels, may be first determined a priori based on experience and patient-specific audiogram data first and then may be fine-tuned during fitting based on patient feedback so as to provide for an optimized individual adjustment of the weights of electric and acoustic stimulation for different situations.

Preferably, the fitting device system comprises a graphical user interface which identifies and displays for given stimulation program, like in the example of FIG. 10, the respective areas in a diagram of the input level versus frequencies of the frequency bands where acoustic stimulation is predominant and where electric stimulation is predominant by displaying the value of the cross-over level as a function of frequency and by displaying the value of the input level below which there is neither acoustic nor electric stimulation as a function of frequencies.

Alternatively or in addition the graphical user interface may display, for a given stimulation program, for each frequency band the total loudness resulting from acoustic stimulation in an electric stimulation as a function of the input level and the partial loudness resulting from acoustic stimulation alone and from electric stimulation alone, respectively, as a function of the input level, as in the example of FIG. 8.

In FIG. 1 the bimodal stimulation system is schematically shown together with an example of a fitting system, comprising a fitting/programming unit 13, which may be implemented as a computer, including a screen 31, and a programming interface 15. The programming unit 13 communicates with the sound processor via the programming interface 15, which may be implemented as a wired or wireless connection (alternatively, there may be separate programming interfaces for electric and acoustic stimulation). It is to be understood that the programming unit 13 is used with the sound processor 24 only for adjustment/fitting, but not during normal operation of the sound processor 24. A fitting system typically has a graphical user interlace, such as the screen 31, which allows the audiologist to see the characteristic audiometric data of the patient, such as the hearing threshold level and the most comfortable level for various stimulation frequencies (such audiogram representation is typically used for fitting of acoustic stimulation devices, such as hearing aids) and allows the audiologist to manually adjust the stimulation parameters, such as the I/O curves of the acoustic stimulation for the patient, thereby individually optimizing the respective aided threshold and most comfortable levels.

Figure 10:
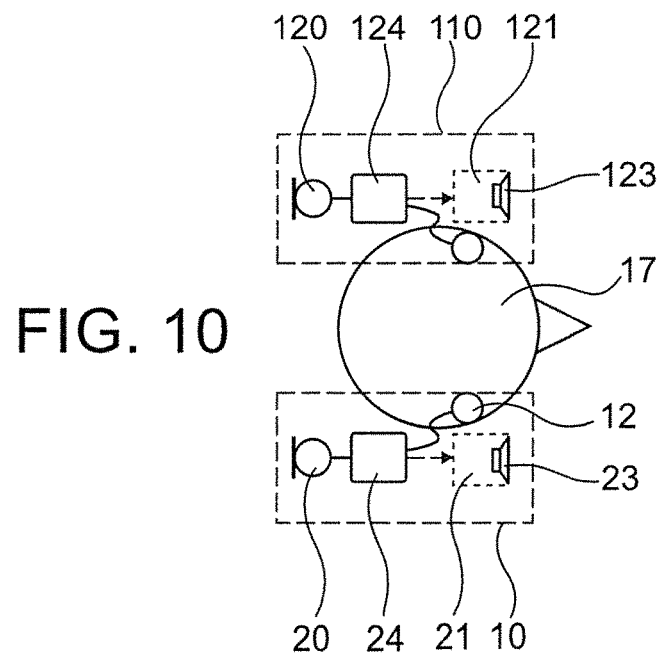
FIG. 10 is a schematic representation of an alternative example of a system to be used in the invention.

According to another example, which is shown in FIG. 10 and which is an alternative to the system shown in FIG. 1, the bimodal system may be designed as a bilateral system, further comprising a second, contralateral EAS device similar 110 to the ipsilateral EAS device 10 and comprising an implantable stimulation assembly 112, an acoustic stimulation unit 121 including a speaker 123 and a sound processor 124 for stimulation of the contralateral ear, wherein the sound processor 24 of the ipsilateral EAS device 10 and the sound processor 124 of the contralateral EAS device 110 communicate with each other via a wired or wireless binaural link so as to bilaterally synchronize the dynamical determining of the relative loudness weight of the electric stimulation and the relative loudness weight of the acoustic stimulation for each frequency band, whereby binaural cues required for auditory localization may be preserved.

While according to the examples described so far the neural stimulation device may be a cochlear implant for electric stimulation of the (ipsilateral) cochlea, it could be, alternatively, any other device for neural hearing stimulation, such as cochlear implant for optical stimulation of the cochlea or an auditory brainstem implant.

The acoustic stimulation device is an acoustic stimulation device in the sense that it provides for vibrational stimulation of the ipsilateral and/or the contralateral ear; for example, it may be, as in the above examples, an electro-acoustic hearing aid comprising a loudspeaker as the output transducer, a bone conduction hearing aid, a middle ear implant (MEI) or a direct acoustic cochlea stimulator (DACS).

The invention claimed is:

1. A bimodal hearing stimulation system comprising:
    an implantable stimulation assembly for applying neural stimulation to a patient's hearing according to an electrical stimulation signal;
    an acoustic stimulation unit for applying acoustic stimulation to the patient's hearing according to an acoustic stimulation signal; and
    a sound processor for generating the electric stimulation signal and the acoustic stimulation signal from an input audio signal,
    wherein the sound processor is configured to divide the input audio signal into a plurality of frequency bands, wherein the sound processor comprises a weighting unit for dynamically determining for each of the frequency bands a weighting function specifying a relative loudness weight of the electric stimulation and a relative loudness weight of the acoustic stimulation as a function of the present level of the input audio signal in the respective frequency band, and wherein the sound processor is configured to apply the weighting function when generating the electric stimulation signal and the acoustic stimulation signal;
    wherein the sound processor is configured to select one stimulation program from a plurality of stimulation programs according to a present acoustic situation, and wherein the weighting function depends on the presently selected stimulation program; and
    wherein in at least one of the stimulation programs the weighting function for a bimodal group comprising at least some of the frequency bands is such that, in terms of loudness, at input levels below a crossover level of the respective frequency band there is predominantly electric stimulation and at input levels above the crossover level there is predominantly acoustic stimulation.

2. The system of claim 1, wherein the weighting function for said bimodal group of the frequency bands is such that in each of the frequency bands of the bimodal group, in terms of loudness, at least at input levels below a first threshold level, which is lower than the crossover level, the acoustic stimulation is zero and at least at input levels above a second threshold level, which higher than the crossover level, the electric stimulation is zero.

3. The system of claim 2, wherein the first and second threshold levels define a level crossover range in which, in terms of loudness, the electric stimulation decreases and the acoustic stimulation increases when the input level increase from the first threshold level to the second threshold level, and wherein at the crossover level the loudness of the acoustic stimulation and the level of the electric stimulation is the same.

4. The system of claim 3, wherein the weighting function is such that within the level crossover range the total loudness resulting from electric stimulation and acoustic stimulation is a monotonous function of the input level.

5. The system of claim 2, wherein at least for some input levels above the second threshold level there is inaudible electric stimulation so as to support acoustic stimulation.

6. The system of claim 1, wherein the bimodal group consists of adjacent frequency bands having frequencies above a first threshold frequency.

7. The system of claim 6, wherein the weighting function for an acoustic-only group consisting of frequency bands having frequencies below the first threshold frequency is such that, in terms of loudness, there is only acoustic stimulation but no audible electric stimulation.

8. The system of claim 7, wherein in the acoustic-only group at least for some input levels there is inaudible electric stimulation so as to support acoustic stimulation.

9. The system of claim 6, wherein the frequencies of the frequency bands of the bimodal group are below a second threshold frequency, and wherein the weighting function for an electric-only group consisting of frequency bands having frequencies above the second threshold frequency is such that, in terms of loudness, there is only electric stimulation but no audible acoustic stimulation.

10. The system of claim 1, wherein one of the stimulation programs is a music program which is to be selected for music input, wherein for at least some of the frequency bands, compared to a speech program which is to be selected for speech input, the relative loudness weight of the acoustic stimulation is increased and the relative loudness weight of the electric stimulation is reduced accordingly.

11. The system of claim 1, wherein at least one of the stimulation programs comprises a feedback elimination feature, wherein in frequency bands for which residual feedback is detected by the sound processor which cannot be suppressed by acoustic feedback cancelation the crossover level is increased and thus, the relative loudness weight of the electric stimulation is increased accordingly, compared to the situation when no residual acoustic feedback is detected.

12. The system of claim 11, wherein the feedback elimination feature reduces the relative loudness weight of the acoustic stimulation at least temporarily to zero.

13. The system of claim 1, wherein one of the stimulation programs is a low battery program which is to be selected for low battery states of the system, wherein, compared to other stimulation programs, at least in some of the frequency bands the relative loudness weight of the electric stimulation is reduced to zero for all input levels and the relative loudness weight of the acoustic stimulation is increased accordingly.

14. The system of claim 1, wherein the sound processor comprises a classifier unit for automatically determining a present acoustic situation by analyzing the input audio signal so as to automatically select the present stimulation program.

15. A system comprising:
    an implantable stimulation assembly for applying neural stimulation to a patient's hearing according to an electrical stimulation signal;
    an acoustic stimulation unit for applying acoustic stimulation to the patient's hearing according to an acoustic stimulation signal;
    a sound processor for generating the electric stimulation signal and the acoustic stimulation signal from an input audio signal, wherein the sound processor is configured to divide the input audio signal into a plurality of frequency bands, wherein the sound processor comprises a weighting unit for dynamically determining for each of the frequency bands a weighting function specifying a relative loudness weight of the electric stimulation and a relative loudness weight of the acoustic stimulation as a function of the present level of the input audio signal in the respective frequency band, and wherein the sound processor is configured to apply the weighting function when generating the electric stimulation signal and the acoustic stimulation signal; and a fitting device communicating with the sound processor, wherein the fitting device is configured to determine crossover levels in a patient-specific manner depending on an individual hearing loss, an available acoustic gain and a feedback margin in the respective frequency band.

16. The system of claim 15, wherein the fitting device is configured to determine the feedback margin via an open-loop gain measurement.

17. The system of claim 15, wherein the fitting device is configured to optimize the crossover levels by fine tuning based on patient feedback.

18. A method for bimodal hearing stimulation of a patient, comprising:
providing an input audio signal;
dividing the input audio signal into a plurality of frequency bands;
generating an electric stimulation signal for applying neural stimulation to the patient's hearing and an acoustic stimulation signal for applying acoustic stimulation to the patient's hearing;
dynamically determining, for each of the frequency bands, a weighting function specifying a relative loudness weight of the electric stimulation and a relative loudness weight of the acoustic stimulation for the respective frequency band as a function of the present level of the input audio signal in the respective frequency band;
applying hearing stimulation to the patient in conformity with the relative loudness weights;
selecting one stimulation program from a plurality of stimulation programs according to a present acoustic situation, and wherein the weighting function depends on the presently selected stimulation program;
wherein in at least one of the stimulation programs the weighting function for a bimodal group comprising at least some of the frequency bands is such that, in terms of loudness, at input levels below a crossover level of the respective frequency band there is predominantly electric stimulation and at input levels above the crossover level there is predominantly acoustic stimulation.

19. A bimodal hearing stimulation system comprising:
an implantable stimulation assembly for applying neural stimulation to a patient's hearing according to an electrical stimulation signal;
an acoustic stimulation unit for applying acoustic stimulation to the patient's hearing according to an acoustic stimulation signal; and
a sound processor for generating the electric stimulation signal and the acoustic stimulation signal from an input audio signal,
wherein the sound processor is configured to divide the input audio signal into a plurality of frequency bands, wherein the sound processor comprises a weighting unit for dynamically determining for each of the frequency bands a weighting function specifying a relative loudness weight of the electric stimulation and a relative loudness weight of the acoustic stimulation as a function of the present level of the input audio signal in the respective frequency band, and wherein the sound processor is configured to apply, in each of the frequency bands, the weighting function when generating the electric stimulation signal and the acoustic stimulation signal by multiplying the relative loudness weight of the electric stimulation to an input/output curve of the electric stimulation, which is stimulation current applied by the implantable stimulation assembly as a function of the level of the input audio signal, and by multiplying the relative loudness weight of the acoustic stimulation to an input/output curve of the acoustic stimulation, which is the acoustic output level of the acoustic stimulation unit as a function of the level of the input audio signal.

* * * * *